(12) United States Patent
Scarpaci

(10) Patent No.: US 9,746,417 B2
(45) Date of Patent: *Aug. 29, 2017

(54) METHOD AND APPARATUS FOR DETERMINING CONCENTRATION USING POLARIZED LIGHT

(71) Applicant: DEKA Products Limited Partnership, Manchester, NH (US)

(72) Inventor: Jacob W. Scarpaci, Manchester, NH (US)

(73) Assignee: DEKA Products Limited Partnership, Manchester, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/243,233

(22) Filed: Aug. 22, 2016

(65) Prior Publication Data

US 2016/0356701 A1 Dec. 8, 2016

Related U.S. Application Data

(63) Continuation of application No. 14/550,182, filed on Nov. 21, 2014, now Pat. No. 9,423,337, which is a continuation of application No. 13/758,535, filed on Feb. 4, 2013, now Pat. No. 8,902,424, which is a continuation of application No. 13/081,783, filed on Apr. 7, 2011, now Pat. No. 8,368,888, which is a continuation of application No. 12/698,377, filed on Feb. 2, 2010, now abandoned, which is a continuation of application No. 11/936,437, filed on Nov. 7, 2007, now Pat. No. 7,656,527.

(60) Provisional application No. 60/857,392, filed on Nov. 7, 2006.

(51) Int. Cl.
*G01J 4/00* (2006.01)
*G01N 21/21* (2006.01)

(52) U.S. Cl.
CPC ..... *G01N 21/21* (2013.01); *G01N 2201/0683* (2013.01)

(58) Field of Classification Search
CPC .................................. G01J 4/00; G01N 21/21
USPC ......................................................... 356/364
See application file for complete search history.

(56) References Cited

U.S. PATENT DOCUMENTS

| | | | | |
|---|---|---|---|---|
| 3,041,921 A | * | 7/1962 | Pickels ..................... | G01J 4/04 250/225 |
| 3,856,408 A | * | 12/1974 | Hill ........................ | G01N 21/21 250/225 |
| 4,286,843 A | * | 9/1981 | Reytblatt ............. | G02B 5/3025 356/33 |
| 5,788,632 A | * | 8/1998 | Pezzaniti ............... | G01N 21/21 356/368 |
| 6,166,807 A | * | 12/2000 | Kawamura ............... | G01J 4/00 356/364 |

(Continued)

*Primary Examiner* — Roy M Punnoose
(74) *Attorney, Agent, or Firm* — Michelle Saquet Temple

(57) ABSTRACT

An apparatus and method for determining the concentration of chiral molecules in a fluid includes a first polarizer configure to polarize light in substantially a first plane to provide initially polarized light. A second polarizer is capable of polarizing the initially polarized light in a plurality of planes, at least one of the plurality of planes being different from the first plane, to provide subsequently polarized light. One or more receivers are included for measuring an intensity of the subsequently polarized light in one or more of the plurality of planes.

8 Claims, 4 Drawing Sheets

(56) References Cited

U.S. PATENT DOCUMENTS

| | | | | |
|---|---|---|---|---|
| 6,466,320 | B1* | 10/2002 | Kawamura | G01J 4/00 356/364 |
| 6,628,387 | B2* | 9/2003 | Darrow | G01N 21/23 356/336 |
| 6,628,388 | B2* | 9/2003 | Darrow | G01N 21/23 356/336 |
| 7,030,981 | B2* | 4/2006 | Bishop | G01N 21/211 356/365 |
| 7,301,633 | B2* | 11/2007 | Gibbs | G01N 21/21 356/367 |
| 7,656,527 | B2* | 2/2010 | Scarpaci | G01N 21/21 356/364 |
| 7,911,608 | B2* | 3/2011 | Busch | G01J 3/42 250/282 |
| 8,368,888 | B2* | 2/2013 | Scarpaci | G01N 21/21 356/364 |
| 2003/0225321 | A1* | 12/2003 | Cote | A61B 5/14558 600/318 |
| 2005/0128482 | A1* | 6/2005 | Gibbs | G01N 21/21 356/364 |
| 2005/0254113 | A1* | 11/2005 | Cirkel | G02B 27/26 359/259 |
| 2015/0157246 | A1* | 6/2015 | Leszinske | G01N 21/21 600/316 |

* cited by examiner

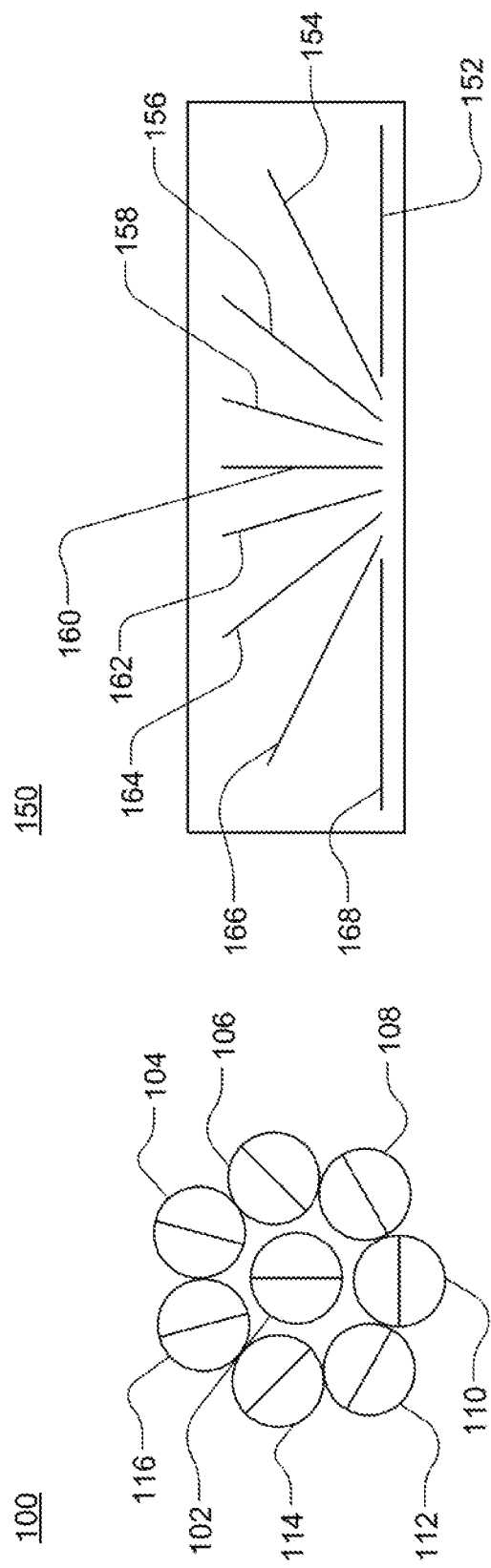

METHOD AND APPARATUS FOR DETERMINING CONCENTRATION USING POLARIZED LIGHT

RELATED APPLICATION(S)

This application is a Continuation of U.S. patent application Ser. No. 14/550,182, filed Nov. 21, 2014 and entitled Method and Apparatus for Determining Concentration Using Polarized Light, now U.S. Pat. No. 9,423,337, issued Aug. 23, 2016, which is a Continuation of U.S. patent application Ser. No. 13/758,535, filed Feb. 4, 2013 and entitled Method and Apparatus for Determining Concentration Using Polarized Light, now U.S. Pat. No. 8,902,424, issued Dec. 2, 2014, which is a Continuation of U.S. patent application Ser. No. 13/081,783 filed on Apr. 7, 2011, and entitled Method and Apparatus for Determining Concentration Using Polarized Light, now U.S. Pat. No. 8,368,888, issued Feb. 5, 2013, which is a Continuation of U.S. patent application Ser. No. 12/698,377 filed on Feb. 2, 2010, and entitled Method and Apparatus for Determining Concentration Using Polarized Light, now abandoned, which is a Continuation of U.S. patent application Ser. No. 11/936,437, filed Nov. 7, 2007 and entitled Method and Apparatus for Determining Concentration Using Polarized Light, now U.S. Pat. No. 7,656,527, issued Feb. 2, 2010, which claims priority from U.S. Provisional Patent Application Ser. No. 60/857,392, filed on Nov. 7, 2006 and entitled Apparatus and Method for Determining Glucose Concentration Using Polarized Light, each of which is hereby incorporated herein by reference in its entirety.

FIELD OF THE DISCLOSURE

The present disclosure relates to determining concentration of chiral molecules in a fluid, and more particularly to determining concentration of chiral molecules in a fluid using polarized light.

BACKGROUND

There are multiple reasons to detect the concentration of a compound in a solution. One reason for detecting concentration may be to ensure proper mixing of multi-component solutions. In order to increase the shelf life of a solution, in some circumstances, the various components may, for example, be kept in different chambers of a multi-chamber solution bag. The seal between the two chambers is then broken, mixing the various components. The concentration of the mixed solution can be used as an indicator to ensure that the chambers have been properly mixed.

Additionally, online mixing of two concentrations of a solution may be carried out to achieve a desired concentration. Automatically detecting the concentrations of solutions as well as creating and verifying a desired concentration, may allow for customized concentrations of solutions to be created, for example, without necessitating a premixed solution having the desired concentration. The ability to detect the available concentrations and to mix different concentrations may be used in a number of different applications.

In various additional circumstances, the concentration of glucose in a solution, or determination of the mere presence of glucose may be desired.

SUMMARY OF DISCLOSURE

In a first implementation an apparatus includes a first polarizer configured to polarize light substantially in a first plane. A second polarizer is configured to polarize light in a plurality of planes, at least one of the plurality of planes being different from the first plane. The apparatus further includes one or more receivers capable of measuring an intensity of incident light transmitted through the first polarizer and through the second polarizer.

One or more of the following features may be included. The apparatus may include a light source capable of providing light incident upon the first polarizer, the light incident upon the first polarizer may be substantially randomly polarized. The apparatus may also include a fluid chamber, at least a portion of the fluid chamber may be at least partially disposed between the first polarizer and the second polarizer. The fluid chamber may include an at least partially transparent fluid line configured to allow a fluid containing a concentration of chiral molecules to flow through the fluid chamber. The chiral molecules may include glucose molecules.

The second polarizer may include a polarizer array including one or more polarizing elements. Each of the one or more polarizing elements may be configured to polarize light substantially in a respective single plane. Each of the respective single planes may be different from one or more of the other of the respective single planes. The second polarizer may include a gradient polarizer configured to polarize light in a plurality of different planes.

At least one of the one or more receivers may be capable of measuring an intensity of light in one or more of the plurality of planes. The receiver may include a linear receiver array. Additionally/alternatively the receiver may include one or more individual receivers, at least one individual receiver associated with each of the plurality of planes.

According to a second implementation, a method includes polarizing light in substantially a first plane to provide initially polarized light, and transmitting the initially polarized light through a fluid chamber. The initially polarized light transmitted through the fluid chamber is polarized in a plurality of planes, at least one of the plurality of planes being different from the first plane, to provide subsequently polarized light. An intensity of the subsequently polarized light is measured in one or more of the plurality of planes.

One or more of the following features may be included. A fluid containing a concentration of chiral molecules may be provided in the fluid chamber. The chiral molecules may include glucose molecules.

The method may include measuring an intensity of the subsequently polarized light when the fluid chamber does not contain the fluid and measuring an intensity of the subsequently polarized light when the fluid chamber contains the fluid. A measured intensity of the subsequently polarized light when the fluid chamber does not contain the fluid and a measured intensity of the subsequently polarized light when the fluid chamber contains the fluid may be compared. The concentration of the chiral molecules may be determined based upon, at least in part, a difference in the measured intensity of the subsequently polarized light when the fluid chamber does not contain the fluid and the measured intensity of the subsequently polarized light when the fluid chamber contains the fluid.

The method may further include providing a visual indicator of measured intensity of the subsequently polarized light in one or more of the plurality of planes. The visual indicator may include a curve of measured intensity of the subsequently polarized light in one or more of the plurality of planes.

The details of one or more implementations are set forth in the accompanying drawings and the description below. Other features and advantages will become apparent from the description, the drawings, and the claims.

BRIEF DESCRIPTION OF THE DRAWINGS

FIG. 3 diagrammatically depicts a polarizer array that may be used in connection with the concentration determining apparatus of FIG. 1;

FIG. 4 diagrammatically depicts a gradient polarizer that may be used in connection with the concentration determining apparatus of FIG. 1.

DETAILED DESCRIPTION OF PREFERRED EMBODIMENTS

Figure 1:
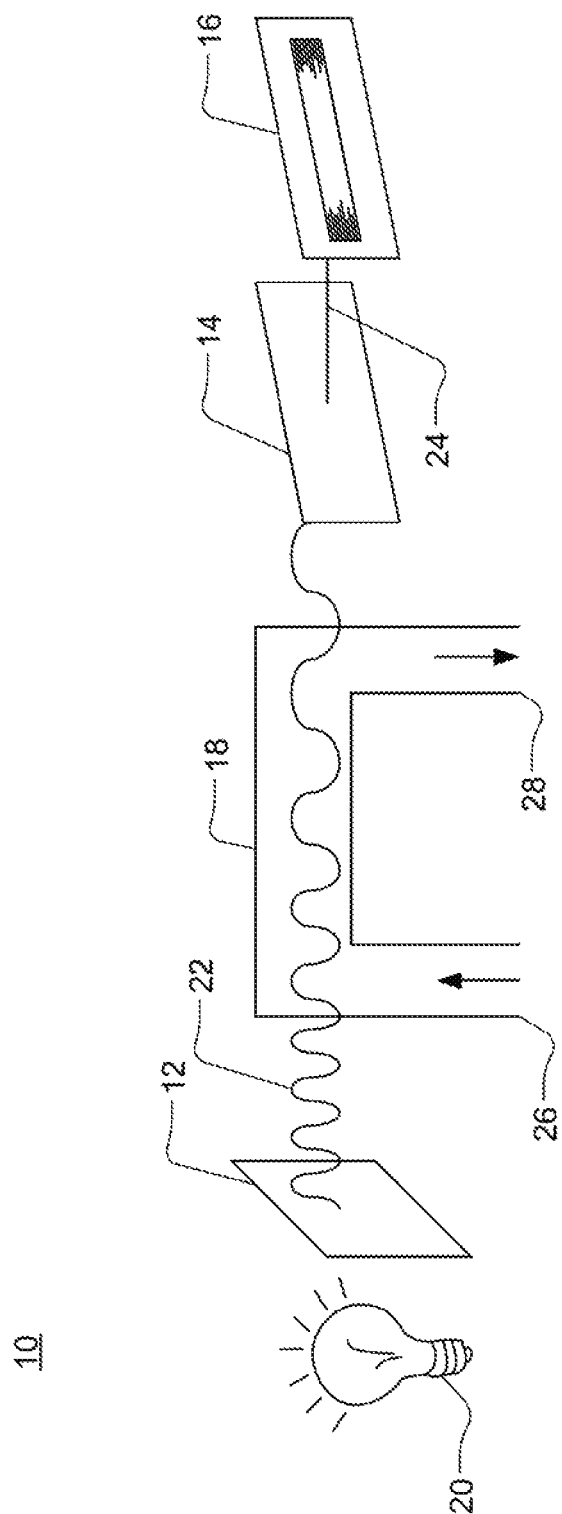
FIG. 1 is a diagrammatic view of a concentration determining apparatus.

Referring to FIG. 1, there is shown concentration determining apparatus 10 for determining the concentration of chiral molecules in a fluid using polarized light. Concentration determining apparatus 10 may include first polarizer 12 configured to polarize light substantially in a first plane. Concentration determining apparatus 10 may additionally include second polarizer 14 configured to polarize light in a plurality of planes, with at least one of the plurality of planes being different from the first plane. Additionally, concentration determining apparatus 10 may include one or more receivers (e.g., receiver 16) capable of measuring an intensity of light transmitted through first polarizer 12 and second polarizer 14.

Fluid chamber 18 capable of containing a fluid including a concentration of chiral molecules may be disposed relative to first polarizer 12 and second polarizer 14, such that at least a portion of fluid chamber 18 is at least partially disposed between first polarizer 12 and second polarizer 14. A concentration of the chiral molecules included within the fluid may be determined based upon, at least in part, an intensity of the light measured by the one or more receivers (e.g., receiver 16).

Figure 2:
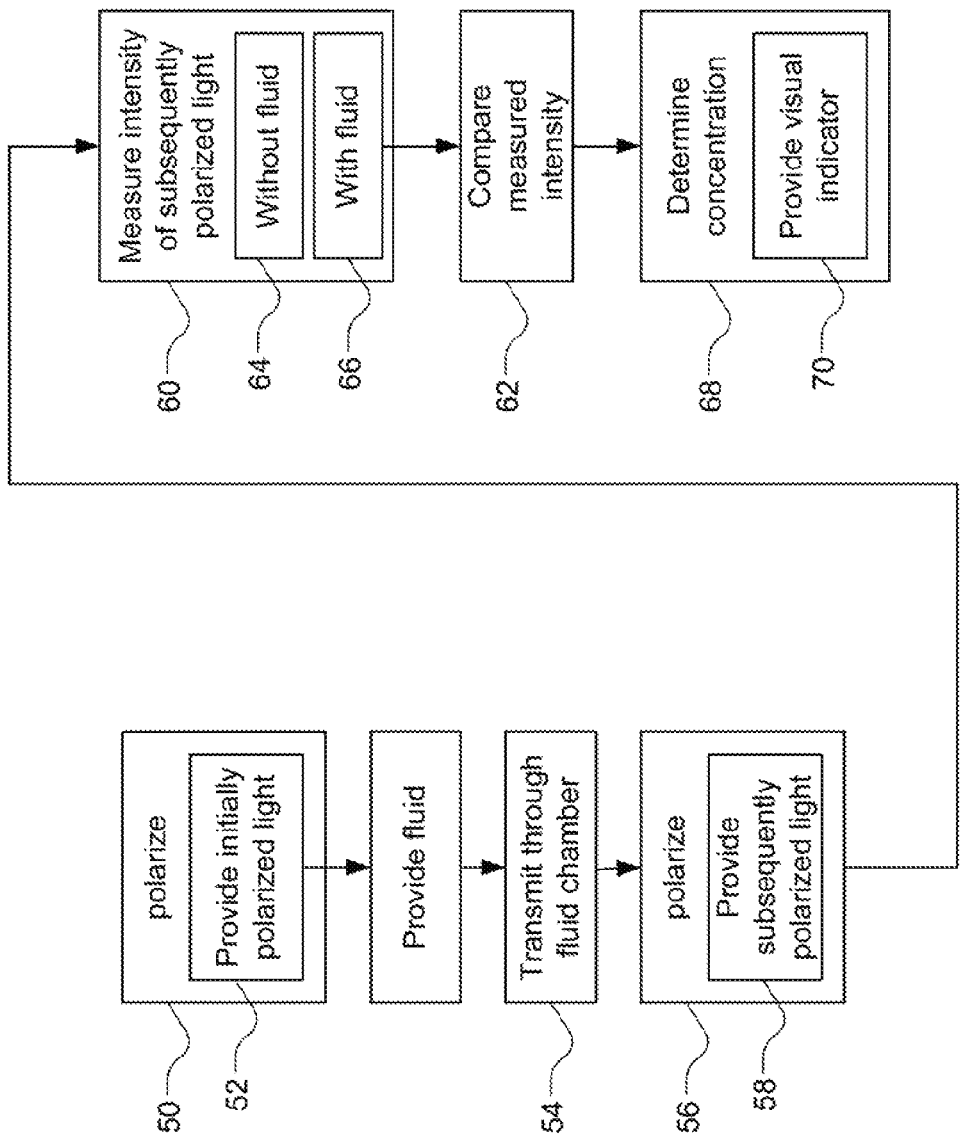
FIG. 2 is a flow chart of a method for determining the concentration of chiral molecules using the concentration determining apparatus of FIG. 1.

Light source 20 may be capable of providing generally randomly polarized light incident upon first polarizer 12. Continuing with the above-stated example, and referring also to FIG. 2, first polarizer 12 may polarize 50 light from light source 20 in substantially a first plane (e.g., in the horizontal plane, as shown in FIG. 1) to provide 52 initially polarized light 22. First polarizer 12 may include any known linear polarizer, such as a polarized film, a polarizing filter, or the like. Initially polarized light 22 transmitted from first polarizer 12 may be transmitted 54 through at least a portion of fluid chamber 18. Second polarizer 14 may polarize 56 initially polarized light 22 transmitted 54 through fluid chamber 18, in a plurality of planes. At least one of the plurality of planes may be different than the first plane (e.g., may be a plane other than the horizontal plane of initially polarized light 22). As such, second polarizer 14 may provide 58 subsequently polarized light 24. Subsequently polarized light 24 may include light polarized in the plurality of planes. That is, subsequently polarized light 24 may include components of initially polarized light 22 oriented in each of the plurality of planes provided by second polarizer 14. Subsequently polarized light 24 associated with each of the plurality of planes may be at least partially spatially separated from subsequently polarized light 24 associated with each of the other planes of the plurality of planes.

Referring also to FIG. 3, second polarizer 14 may include polarizer array 100. Polarizer array 100 may include one or more individual polarizing elements (e.g., polarizing elements 102, 104, 106, 108, 110, 112, 114, 116). Each of polarizing elements 102, 104, 106, 108, 110, 112, 114, 116 may be configured to polarize 56 initially polarized light 22 substantially in a respective single plane. Each of the respective single planes may be different from one or more of the other respective single planes. For example, as shown, each of polarizing elements 102, 104, 106, 108, 110, 112, 114, 116 may have a polarization plane (e.g., diagrammatically indicated by the bisecting line of each polarizing element 102, 104, 106, 108, 110, 112, 114, 116) that is different from each of the other polarizing elements 102, 104, 106, 108, 110, 112, 114, 116. For example, as shown, polarizing element 102 may have a generally vertical polarizing plane. The polarization plane of each of polarizing elements 104, 106, 108, 110, 112, 114, 116 may be incrementally rotated 22.5 degrees relative to the angularly adjacent polarizing elements. Of course other incremental rotational angles, as well as varying numbers of polarizing elements may be used depending upon preference and design criteria. Further, one or more of the polarizing elements may additionally/alternatively have a polarization plane that is the same as one or more of the other polarizing elements.

Referring also to FIG. 4, second polarizer 14 may also include gradient polarizer 150. Gradient polarizer 150, which may be formed, e.g., via photolithography, or other suitable techniques, may be configured to polarize light in a plurality of different planes, diagrammatically represented by polarizing axes 152, 154, 156, 158, 160, 162, 164, 166, 168. Gradient polarizer 150 may include incremental polarization planes, or may include continuously varying polarization planes. Gradient polarizer 150 may provide a plurality of polarization planes within a small area, e.g., which may reduce the size of second polarizer 14.

As mentioned above, subsequently polarized light 24 associated with each of the plurality of planes may be at least partially separated from subsequently polarized light 24 associated with each of the other planes of the plurality of planes. In the example of polarizer array 100, each polarizing element 102, 104, 106, 108, 110, 112, 114, 116 may provide 58 subsequently polarized light 24 associated with one of the plurality of planes (e.g., having a different plane of polarization). As shown, polarizing elements 102, 104, 106, 108, 110, 112, 114, 116 are at least partially spatially separated from one another. Subsequently polarized light 24 associated with each of polarizing elements 102, 104, 106, 108, 110, 112, 114, 116 may be similarly at least partially spatially separated from one another. In a similar manner, gradient polarizer 150 may provide subsequently polarized light 24 associated with each of the plurality of planes (e.g., represented by polarizing axes 152, 154, 156, 158, 160, 162, 164, 166, 168) that may be at least partially linearly separated from subsequently polarized light 24 associated with each of the other of the plurality of planes.

Continuing with the above-stated example, the one or more receivers (e.g., receiver 16) may measure 60 the intensity of subsequently polarized light 24 in one or more of the plurality of planes provided by second polarizer 14. The one or more receivers (e.g., receiver 16) may include a linear receiver array (e.g., a CMOS sensor array), in which a respective portion of the linear receiver array may measure 60 the intensity of subsequently polarized light 24 corresponding to a specified one (or range) of the plurality of planes. For example, as discussed above, second polarizer 14 may polarize initially polarized light 22 in a plurality of planes. A region of a linear receiver array may measure the intensity of subsequently polarized light 24 associated with each of the plurality of planes. In a further embodiment, the one or more receivers may include a separate receiver for each of the plurality of planes (or a range of the plurality of planes) provided by second polarizer 14.

The intensity of the light measured 60 by the one or more receivers may be based upon, at least in part, the difference between the angle of the first plane of initially polarized light 22 and the angles of each of the plurality of planes of polarization provided by second polarizer 14. Generally, an angular difference between the first plane and a respective one of the plurality of planes provided by second polarizer 14 approaching 90 degrees may provide a lower measured 60 intensity associated with the respective one of the plurality of planes. The intensity of the measured light 60 associated with one of the plurality of planes provided by second polarizer 14 may be given by:

$$M_{post} = M_{pre} k |\cos(\theta \text{diff})|$$

wherein $M_{pre}$ is the magnitude of the intensity of initially polarized light 22, $M_{post}$ is the magnitude of the intensity of subsequently polarized light 24 associated with the respective one of the plurality of planes provided by second polarizer 14, k is an attenuation factor of second polarizer 14, e.g., which may account for losses during transmission of initially polarized light 22 through second polarizer 14, and θ diff is the angular difference between the first plane and the respective one of the plurality of planes provided by second polarizer 14. Accordingly, a maximum intensity may be measured 60 when θ diff is equal to zero degrees, and a minimum intensity may be measured 60 when θ diff is equal to 90 degrees.

As mentioned above, at least a portion of fluid chamber 18 may be at least partially disposed between first polarizer 12 and second polarizer 14. Fluid chamber 18 may include an at least partially transparent fluid line configured to allow a fluid containing a concentration of chiral molecules to flow through fluid chamber 18 (e.g., via inlet 26 and outlet 28). Additionally, the at least partially transparent fluid line may allow for the transmission 54 of initially polarized light 22 through fluid chamber 18 and any at least partially transparent fluid contained therein. Fluid chamber 18 may be a disposable component, e.g., associated with a fluid source (not shown) and/or a fluid delivery system (also not shown). Concentration determining apparatus may allow optical detection of the concentration of the chiral molecules. As such, the concentration of the chiral molecules may be determined without direct contact with the fluid.

An example of a chiral molecule may include, but is not limited to, glucose. For example, the fluid may include a dialysate including glucose. Based upon, at least in part, the chirality of glucose, polarized light (e.g., initially polarized light 22) transmitted 54 through the dialysate may be rotated by the glucose. The angle of rotation of the polarized light may vary generally linearly with the length of the path of the polarized light through the fluid and the concentration of the chiral molecule within the fluid. As such, the concentration of glucose in the dialysate may be determined based upon, at least in part, the length of the path through the dialysate and the angular rotation of polarized light passing through the dialysate. The relationship between the angle of rotation, the length of the path of the polarized light and the concentration of the chiral molecule in the fluid may be given by:

$$\phi = \alpha_\lambda L C$$

wherein φ is the angle of rotation of the polarized light, $\alpha_\lambda$ is the specific rotation for the chiral molecule at wavelength λ, L is the path length of the polarized light, and C is the concentration of the chiral molecule within the fluid. The above equation may be similarly applicable to other fluids containing chiral molecules.

Continuing with the above stated example of a dialysate including glucose, glucose may be dextrorotatory. As such, light may be rotated in a right-handed direction when passing through a fluid including glucose. Additionally, the specific rotation may increase as the wavelength of the light decreases. Therefore light with shorter wavelengths may be rotated a greater angle for a given path length through the fluid having a given concentration of glucose. As an example of the specific rotation of glucose, for a wavelength of λ=589 nm, $\alpha_\lambda$=52.6° ml/(dm g). Accordingly, in one embodiment light source 20 may be, e.g., an LED providing substantially randomly polarized light having an approximate wavelength of 589 nm. Of course, other wavelengths may additionally be used depending upon design criteria and preference. Specific rotation may be determined for the wavelength of light source 20, allowing concentration of glucose to be calculated based upon the specific rotation for the wavelength used, the path length through the glucose, and the angle of rotation of polarized light passing through the glucose.

Based upon, at least in part, the specific rotation of the chiral molecules included within the fluid, the path length through the fluid, and an angle of rotation of polarized light passing through the fluid, the concentration of the chiral molecules included within the fluid may be determined according to the above-described relationship. As also discussed above, the angle of the plane of initially polarized light 22 incident upon second polarizer 14 (e.g., after being transmitted 54 through fluid chamber 18) may be determined based upon, at least in part, the measured 60 intensity of the subsequently polarized light in the plurality of planes. The angle of rotation of polarized light passing through the fluid including a concentration of chiral molecules may be determined, at least in part, by comparing 62 the intensity of the subsequently polarized light 24 in the plurality of planes when fluid chamber 18 does not contain the fluid including a concentration of chiral molecules and the intensity of the subsequently polarized light 24 when fluid chamber 18 does contain the fluid including a concentration of chiral molecules (resulting in rotation of initially polarized light 22 transmitted through fluid chamber 18).

Continuing with the above-stated example, measuring 60, by the one or more receivers, the intensity of subsequently polarized light 24 in the plurality of planes provided by second polarizer 14 may include measuring 64 the intensity of subsequently polarized light 24 in the plurality of planes when fluid chamber 18 does not contain the fluid including a concentration of chiral molecules and measuring 66 the intensity of subsequently polarized light 24 in the plurality of planes when fluid chamber 18 does contain the fluid including a concentration of chiral molecules (e.g., by causing the fluid to flow through fluid chamber 18 via inlet 26 and outlet 28).

Figure 5:
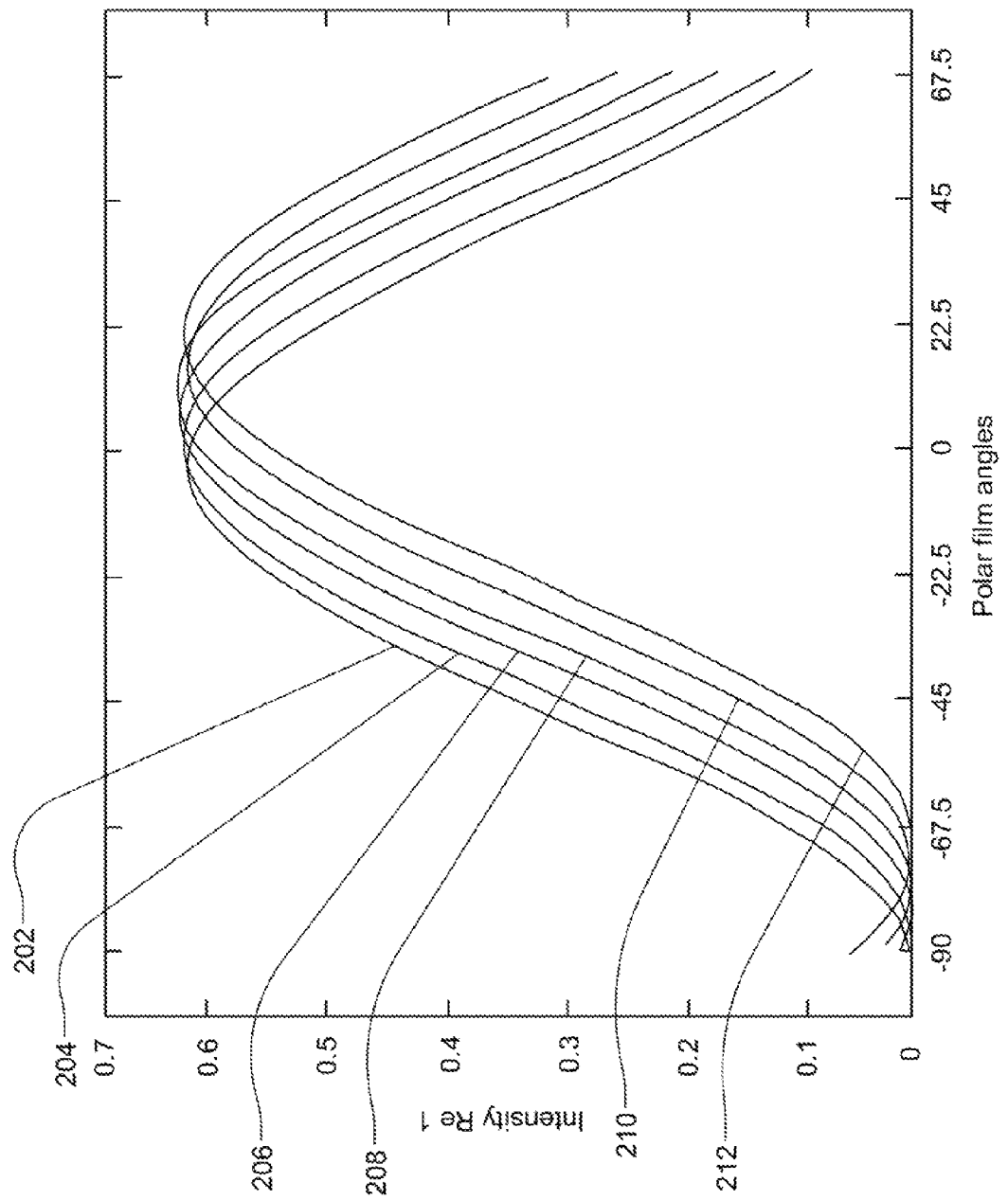
FIG. 5 shows a plot of relative intensity versus polarization plane angle for various rotational angles of initially polarized light.

The concentration of the chiral molecules may be determined 68 based upon, at least in part, a difference in the measured 64 intensity of subsequently polarized light 24 when fluid chamber 18 does not contain the fluid and the measured 66 intensity of subsequently polarized light 24 when fluid chamber 18 contains the fluid. Referring also to FIG. 5, determining 68 the concentration of the chiral molecules included within the fluid may include providing a visual indicator of measured 60 intensity of subsequently polarized light at one or more of the plurality of planes. For example, plot 200 may correlate the relative intensity of subsequently polarized light 24 to the angle of each of the plurality of planes. Curve 202 may be fit to the measured 64 intensity of subsequently polarized light of each of the plurality of planes when fluid chamber 18 does not include the fluid. The peak of curve 202 may correspond to the angle of initially polarized light 22 incident upon second polarizer 14 (e.g., after passing through fluid chamber 18 when fluid chamber 18 does not contain the fluid including chiral molecules).

In a similar manner, curves 204, 206, 208, 210, and 212 may correspond to rotation angles of 5, 10, 15, 20, and 25 degrees of initially polarized light 22 relative to second polarizer 14 (e.g., as may occur when initially polarized light 22 passes through the fluid including chiral molecules of increasing concentration, when fluid chamber 18 does contain the fluid including a concentration of chiral molecules). As with curve 202, the peak of curves 204, 206, 208, 210, and 212 may correspond to the angle of initially polarized light 22 incident upon second polarizer 14, e.g., as may occur after passing through fluid chamber 18 when fluid chamber 18 does contain the fluid including a concentration of chiral molecules. The offset of curves 204, 206, 208, 210, 212 relative to curve 202 may indicate the angle of rotation of initially polarized light 22, for example as may be imparted by the fluid including a concentration of chiral molecules. As discussed above, the concentration of chiral molecules included within the fluid may be calculated based upon the path length of initially polarized light 22 through the fluid including chiral molecules and the angle of initially polarized light 22 incident upon second polarizer 14 after passing through fluid including a concentration of chiral molecules (e.g., as compared to the angle of initially polarized light 22 incident upon second polarizer 14 after passing through fluid chamber 18 not containing the fluid including a concentration of chiral molecules).

According to one aspect, concentration determining apparatus 10 may be calibrated, e.g., to account for any gain associated with the one or more receivers. For example, un-polarized (e.g., randomly polarized) light incident on second polarizer 14 may produce subsequently polarized light 24 having a generally equal intensity in each of the plurality of planes. The one or more receivers (e.g., receiver 16) may measure 60 the intensity of subsequently polarized light 24 (resulting from non-polarized light incident on second polarizer 14) in each of the plurality of planes. A gain factor may be determined for each of the one or more receivers (e.g., for each of the plurality of planes) so that the measured intensity for each of the plurality of planes may be adjusted to provide a generally uniform measured intensity in each of the plurality of planes. The gain factor determined for each of the one or more receivers may be applied to measured 60 intensities for each respective one of the one or more receivers to factor out the gain associated with each of the one or more receivers.

A number of implementations have been described. Nevertheless, it will be understood that various modifications may be made. Accordingly, other implementations are within the scope of the following claims.

What is claimed is:

1. A method for determining the concentration of chiral molecules in a fluid comprising:
   transmitting initially polarized light through a fluid chamber;
   polarizing the initially polarized light transmitted through the fluid chamber in at least a first plane and a second plane, the second plane being different from the first plane, to provide subsequently polarized light;
   measuring an intensity of the subsequently polarized light in the at least two planes; and
   determining the concentration of chiral molecules in the fluid using the measured intensity of the subsequently polarized light.

2. The method of claim 1, further including providing a fluid capable of containing a concentration of chiral molecules in the fluid chamber.

3. The method of claim 2, wherein the chiral molecules include glucose molecules.

4. The method of claim 2, further including measuring an intensity of the subsequently polarized light when the fluid chamber does not contain the fluid and measuring an intensity of the subsequently polarized light when the fluid chamber contains the fluid.

5. The method of claim 4, further including comparing a measured intensity of the subsequently polarized light when the fluid chamber does not contain the fluid and a measured intensity of the subsequently polarized light when the fluid chamber contains the fluid.

6. The method of claim 5, further including determining the concentration of the chiral molecules based upon, at least in part, a difference in the measured intensity of the subsequently polarized light when the fluid chamber does not contain the fluid and the measured intensity of the subsequently polarized light when the fluid chamber contains the fluid.

7. The method of claim 6, further including providing a visual indicator of measured intensity of the subsequently polarized light in one or more of the plurality of planes.

8. The method of claim 7, wherein the visual indicator includes a curve of measured intensity of the subsequently polarized light in one or more of the plurality of planes.

* * * * *